(12) United States Patent
Humphreys et al.

(10) Patent No.: US 7,205,274 B2
(45) Date of Patent: Apr. 17, 2007

(54) HYBRID PEPTIDES MODULATE THE IMMUNE RESPONSE

(75) Inventors: Robert E. Humphreys, Acton, MA (US); Sharlene Adams, Watertown, MA (US); Minzhen Xu, Northborough, MA (US)

(73) Assignee: Antigen Express, Inc., Worcester, MA (US)

( * ) Notice: Subject to any disclaimer, the term of this patent is extended or adjusted under 35 U.S.C. 154(b) by 440 days.

(21) Appl. No.: 10/197,000

(22) Filed: Jul. 17, 2002

(65) Prior Publication Data

US 2003/0091582 A1    May 15, 2003

Related U.S. Application Data

(62) Division of application No. 09/396,813, filed on Sep. 14, 1999, now Pat. No. 6,432,409.

(51) Int. Cl.
*A61K 38/00* (2006.01)
*A61K 39/385* (2006.01)

(52) U.S. Cl. .............. 514/2; 514/12; 514/13; 424/184.1; 424/185.1; 424/192.1; 424/193.1

(58) Field of Classification Search .......... 514/2, 514/12, 13; 424/184.1, 185.1, 192.1, 193.1
See application file for complete search history.

(56) References Cited

U.S. PATENT DOCUMENTS 5,559,028 A    9/1996    Humphreys
5,827,516 A    10/1998   Urban et al.
5,919,639 A    7/1999    Humphreys et al.

FOREIGN PATENT DOCUMENTS

WO    WO 98/37178    8/1998

OTHER PUBLICATIONS

Adams and Humphreys, Eur. J. Immunol. 25: 1693-1702 (1995).
Adams et al., Arzneim.-Forsch./Drug Res. 47: 1069-1077 (1997).
Stern et al., Nature 378: 215-221 (1994).
Ghosh et al., Nature 378: 457-462 (1995).
Xu et al., Arzneim.-Forsch./Drug Res. 49: 791-799 (1999).
Sanderson et al., PNAS 92: 7217-7221 (1995).

*Primary Examiner*—Christina Chan
*Assistant Examiner*—F. Pierre vanderVegt
(74) *Attorney, Agent, or Firm*—Pierce Atwood LLP; Kevin M. Farrell; Marjorie Gurganus

(57) ABSTRACT

The present invention provides an MHC class II antigen presentation enhancing hybrid polypeptide. The hybrid has an N-terminus comprising the mammalian Ii key peptide LRMKLPKPPKPVSKMR (SEQ ID NO: 1) and modifications thereof which retain antigen presentation enhancing activity, a C-terminus comprising an antigenic epitope in the form of a polypeptide or peptidomimetic structure which binds to the antigenic peptide binding site of an MHC class II molecule, and an intervening chemical structure covalently linking the N-terminal and C-terminal components.

3 Claims, No Drawings

SEQUENCE LISTING

<160> NUMBER OF SEQ ID NOS: 12

<210> SEQ ID NO 1
<211> LENGTH: 16
<212> TYPE: PRT
<213> ORGANISM: Mouse

<400> SEQUENCE: 1

Leu Arg Met Lys Leu Pro Lys Pro Pro Lys Pro Val Ser Lys Met Arg
1               5                   10                  15

-continued

```
<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence:
      Modified mouse Ii key peptide

<400> SEQUENCE: 2

Tyr Arg Met Lys Leu Pro Lys Pro Pro Lys Pro Val Ser Lys Met Arg
 1               5                  10                  15

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence:
      Modified mouse Ii key peptide

<400> SEQUENCE: 3

Leu Arg Met Lys
 1

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence:
      Modified mouse Ii key peptide

<400> SEQUENCE: 4

Leu Arg Met Lys Leu Pro Lys
 1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence:
      Modified mouse Ii key peptide

<400> SEQUENCE: 5

Leu Arg Met Lys Leu Pro Lys Ser
 1               5

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence:
      Modified mouse Ii key peptide

<400> SEQUENCE: 6

Leu Arg Met Lys Leu Pro Lys Ser Ala Lys Pro
 1               5                  10

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence:
      Modified mouse Ii key peptide
```

-continued

```
<400> SEQUENCE: 7

Leu Arg Met Lys Leu Pro Lys Ser Ala Lys Pro Val Ser Lys
 1               5                  10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence:
      Fusion of spacer sequences and Hornworm moth cytochrome C
      epitope

<400> SEQUENCE: 8

Ile Ala Tyr Leu Lys Gln Ala Thr Ala Lys
 1               5                  10

<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence:
      Fusion of modified Ii key peptide, spacer sequences, and
      Hornworm moth cytochrome C epitope.

<400> SEQUENCE: 9

Leu Arg Met Lys Leu Pro Lys Ser Ile Ala Tyr Leu Lys Gln Ala Thr
 1               5                  10                  15

Ala Lys

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence:
      Fusion of modified Ii key peptide, spacer sequences and
      Hornworm moth cytochrome C epitope.

<400> SEQUENCE: 10

Ile Ala Tyr Leu Lys Gln Ala Thr Ala Lys
 1               5                  10

<210> SEQ ID NO 11
<211> LENGTH: 24
<212> TYPE: PRT
<213> ORGANISM: Artificial Sequence
<220> FEATURE:
<223> OTHER INFORMATION: Description of Artificial Sequence:
      Fusion of modified Ii key peptide, spacer sequences, and
      Hornworm moth cytochrome C epitope

<400> SEQUENCE: 11

Leu Arg Met Lys Leu Pro Lys Ser Ala Lys Pro Val Ser Lys Ile Ala
 1               5                  10                  15

Tyr Leu Lys Gln Ala Thr Ala Lys
            20

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Spacer
      sequences
```

```
-continued

<400> SEQUENCE: 12

Leu Pro Lys Ser Ala Lys Pro Val Ser Lys
 1               5                  10
```

HYBRID PEPTIDES MODULATE THE IMMUNE RESPONSE

BACKGROUND OF THE INVENTION

The immune system responds to foreign pathogens, to tumor cells, to autoimmune disease-inducing processes, to allergens, to grafts, through the recognition of the 'foreign' or 'abnormal' structures, as antigens. Most of those antigens are proteins, which are synthesized either by cells of the host, or by a pathogen. Such antigens are processed (proteolytically digested) into peptide fragments which come to be presented to the responding lymphocytes of the immune system, in a peptide-presenting structure on the surface of the antigen presenting cell. Those peptide presenting structures are called major histocompatibility complex (MHC) molecules. They obtained that name since they were first recognized as products of polymorphic, allelic genes in the MHC locus, which genes control graft rejection among inbred strains of mice.

Animals have developed such complex methods to present and recognize antigens, in order to discriminate peptides derived from 'self' molecules, from peptides derived from 'nonself' molecules. This invention concerns matter and methods to exploit this fundamental process at the first step in the immune response. Here are revealed compounds and methods to enhance the charging of selected antigenic peptides into certain MHC molecules for a vaccination of the immune system. Such a vaccination will enhance toxic responses against foreignness of an invading pathogen, or a tumor. Other methods using compounds of the invention, can be applied to reinforce the recognition of self, to control autoimmune diseases, allergies, or graft rejection.

The immune response to a specific antigen is mediated by T lymphocytes which recognize peptide fragments of those antigens in the MHC molecules. Within an antigen presenting cell (APC), peptide fragments of a proteolytically processed antigen become bound into the antigenic peptide binding site of major histocompatibility complex (MHC) molecules. These peptide-MHC complexes are then transported to the cell surface for recognition (of both the foreign peptide and the adjacent surface of the presenting MHC molecule) by T cell receptors on responding T lymphocytes. Those T lymphocytes can have either immunoregulatory functions (to help or suppress an immune response) or effector functions (to clear the pathogen or tumor, for example, through a cytotoxic immune response). The antigen-specific recognition event initiates the immune response cascade which leads to a protective immune response, or in the case of autoimmune processes, a deleterious immune response.

Two classes of MHC molecules function as immune system presenters of antigenic peptides to T cells. MHC class I molecules receive peptides from endogenously synthesized proteins, such as an infectious virus, in the endoplasmic reticulum about the time of synthesis of the MHC class I molecules. The MHC class I-bound antigenic peptides are presented at the cell surface to CD8-positive cytotoxic T lymphocytes, which then become activated and can directly kill the virus-expressing cells. In contrast, MHC class II molecules are synthesized in the endoplasmic reticulum with their antigenic peptide binding sites blocked by the invariant chain protein (Ii). These complexes of MHC class II molecules and Ii protein are transported from the endoplasmic reticulum to a post-Golgi compartment where Ii is released by proteolysis and a specific antigenic peptide becomes bound to the MHC class II molecule (Blum et al., Proc. Natl. Acad. Sci. USA 85: 3975 (1988); Riberdy et al., Nature 360: 474 (1992); Daibata et al., Mol. Immunol. 31: 255 (1994); Xu et al., Mol. Immunol. 31: 723 (1994); Xu et al., Antigen Processing and Presentation, Academic Press, NY p227 (1994); Kropshofer et al., Science 270: 1357 (1995); and Urban et al., J. Exp. Med. 180: 751 (1994)).

R. Humphreys (1996) U.S. Pat. No. 5,559,028, and Humphreys et al. (1999) U.S. Pat. No. 5,919,639 revealed the mechanisms by which Ii protein is cleaved, releasing fragments in the course of cleavage to regulate the binding and locking in of antigenic peptides within the antigenic peptide binding site of MHC class II molecules (Adams et al., Eur. J. Immunol. 25: 1693 (1995); Adams et al., Arzneim. Forsch./Drug Research 47: 1069 (1997); and Xu et al., Arzneim. Forsch./Drug Research in press (1999)). One segment of the Ii protein, Ii(77–92), was found to act at an allosteric site outside the antigenic peptide binding site near the end of that site holding the N-terminus of the antigenic peptide. The referenced patents, furthermore, disclosed novel therapeutic compounds and methods to control this initial regulatory, antigenic peptide recognizing event of the immune response by three classes of mechanisms. In the first mechanism, antigenic peptides are spilled from cell surface MHC class II molecules by the action of compounds of the invention.

In the second, the charging of the antigenic peptide binding site on those molecules is promoted with compounds of the invention for binding of other, synthetic peptides. Such inserted peptide sequences can be either antigenic epitopes or nonantigenic peptide sequences which nevertheless bind tightly to block the antigenic peptide binding site. The third mechanism involves altering the rates of association/dissociation of antigenic peptides from those complexes and the nature of the interaction of components of the trimolecular MHC molecule/antigenic peptide/T cell receptor complex, and furthermore the interaction of that trimolecular complex with auxiliary cell-to-cell interaction molecules, in a manner to regulate differentiation and function of the responding T lymphocytes.

The present invention reveals the surprising finding that covalent coupling of the Ii-Key peptide homologs with an antigenic peptide leads to a considerable increase in potency of the presentation of the antigenic epitope. Furthermore, the linker between core, biologically active segment of the Ii-Key peptide need not be a particular peptide sequence derived from the Ii protein. Flexible, simple linkers composed, for example, of repeating methylene (—$CH_2$—) groups, are sufficient and preferred.

The compounds and methods of the present invention can be applied as novel therapeutic and diagnostic compounds in various diseases and conditions. By acting at the initial regulatory, antigenic peptide recognizing event of the immune response, these compounds are favored over other therapeutics with various toxic side effects.

Herein, are revealed utilities in 1) the identification of antigenic epitopes of infectious, malignant, autoimmune and allergic diseases and graft rejection, 2) the use of such epitopes for diagnostic purposes, and 3) the use of such epitopes for therapeutic purposes.

SUMMARY OF THE INVENTION

One aspect of the present invention relates to an MHC class II antigen presentation enhancing hybrid polypeptide. The hybrid comprises an N-terminus comprising the mammalian Ii key peptide LRMKLPKPPKPVSKMR (SEQ ID NO: 1) and modifications thereof which retain antigen presentation enhancing activity, a C-terminus comprising an antigenic epitope in the form of a polypeptide or peptidomimetic structure which binds to the antigenic peptide binding site of an MHC class II molecule, and an intervening chemical structure covalently linking the N-terminal and C-terminal components of the hybrid, the chemical structure being a covalently joined group of atoms which when arranged in a linear fashion forms a flexible chain which extends up to the length of 20 amino acids likewise arranged in a linear fashion. In preferred embodiments the intervening chemical structure is unable to hydrogen bond in any spatially distinct manner to the MHC class II molecule, and preferably is the length of about 4 to 6 amino acids likewise arranged in a linear fashion. Modifications of the Ii key peptide used in the hybrid include, deletion of one or more amino acids from the N-terminus, deletion of one or more amino acids from the C-terminus, protection of the N-terminus, amino acid substitution, and generation of cyclized derivatives. In one embodiment, the Ii key peptide used in the hybrid is modified by C-terminal truncation to LRMK (SEQ ID NO: 3). Preferred hybrids of the present invention include Ac-LRMK(SEQ ID NO: 3)-5-aminopentanoyl-IAYLKQATAK(SEQ ID NO: 8)-NH$_2$, Ac-LRMK(SEQ ID NO: 3)-5-aminopentanoyl-5-aminopentanoyl-IAYLKQATAK (SEQ ID NO: 8)-NH$_2$, Ac-LRMKLPKSIAYLKQATAK-NH$_2$ (SEQ ID NO: 9), Ac-LRMKLPKSAKPIAYLKQATAK-NH$_2$ (SEQ ID NO: 10), or Ac-LRMKLPKSAKPVSKIAYLKQATAK-NH$_2$ (SEQ ID NO: 11). Another preferred modification of the Ii key peptide used in the hybrid is a substitution of one or more amino acids with a peptidomimetic structure, a D-isomer amino acid, a N-methyl amino acid, a L-isomer amino acid, a modified L-isomer amino acid, or a cyclized derivative. Methods for identifying a molecule which functions within the context of an MHC class II antigen presentation enhancing hybrid in an equivalent fashion as the Ii key peptide are also presented.

Another aspect of the present invention relates to a method for enhancing presentation of an MHC class II restricted antigenic epitope to a T cell, comprising incorporating the MHC class II restricted antigenic epitope into an MHC class II antigen presentation enhancing hybrid polypeptide of the present invention and then contacting under physiological conditions, the hybrid polypeptide, an MHC class II expressing antigen presenting cell, and a T cell which is responsive to the presentation of the antigenic epitope by an MHC class II molecule of the antigen presenting cell. This method is useful in increasing the MHC class II allelic response to the incorporated antigenic epitope. Antigenic epitopes which exhibit a predetermined pattern of MHC class II restricted Th1 and Th2 stimulation can also be identified more easily when incorporated into a hybrid of the present invention. Hybrids of the present invention are also useful for modulating the immune response of an individual to a specific molecule, by enhancing the MHC class II presentation of an antigenic epitope of the molecule to specified T lymphocytes of the individual. Both in vivo and ex vivo methods are provided.

Another aspect of the present invention relates to a method for generally inhibiting presentation of MHC class II restricted antigenic epitopes to T lymphocytes. The method comprises contacting the following components under physiological conditions: an MHC class II expressing antigen presenting cell displaying on its surface a T lymphocyte-presented antigenic epitope; a T lymphocyte which is responsive to the presentation of the antigenic epitope by an MHC class II molecule of the antigen presenting cell; and an antigen presentation inhibiting hybrid polypeptide comprising i) an N-terminus comprising the mammalian Ii key peptide LRMKLPKPPKPVSKMR (SEQ ID NO: 1) and modifications thereof which retain antigen presentation enhancing activity, ii) a C-terminus comprising an antigen binding site ligand or peptidomimetic structure which binds into the antigenic peptide binding site of an MHC class II molecule, and iii) an intervening chemical structure covalently linking the N-terminal and C-terminal components of the hybrid, the chemical structure being a covalently joined group of atoms which when arranged in a linear fashion forms a flexible chain which extends up to the length of 20 amino acids likewise arranged in a linear fashion. This method is useful for treating an individual for a disease associated with the generation of a non-beneficial immune response, by generally inhibiting MHC class II antigen presentation by antigen presenting cells of the individual. A method for identifying a compound which inhibits MHC class II antigen presentation is also provided.

DETAILED DESCRIPTION OF THE INVENTION

Aspects of the present invention are based on the discovery that an MHC class II restricted antigenic epitope which is covalently linked to a mammalian Ii key peptide by an appropriate intervening chemical structure, to form a hybrid polypeptide, is presented to T lymphocytes by antigen presenting cells with significantly higher efficacy than is the precursor antigenic epitope. The hybrid polypeptide formed is referred to herein as an 'MHC class II antigen presentation enhancing hybrid polypeptide', or more simply as an 'enhancing hybrid'. The enhancing hybrid of the present invention has an N-terminus comprised of a mammalian Ii key peptide, or a modification thereof, which retains antigen presentation enhancing activity, described in more detail below. Covalently linked to the Ii key peptide is the specific antigenic epitope to be presented. Between the Ii key peptide and the antigenic epitope is an intervening chemical structure which covalently links the other two components. This intervening chemical structure is referred to herein as a 'spacer'. Necessary parameters of the spacer are described in more detail below.

It has previously been demonstrated that the mammalian Ii key peptide LRMKLPKPPKPVSKMR (SEQ ID NO: 1), and a modified mammalian Ii-key peptide, YRMKLPKPPKPVSKMR (SEQ ID NO: 2), have the ability to alter presentation of certain MHC class II-restricted, antigenic peptides to T lymphocyte-hybridomas which recognize those respective antigenic peptides (R. Humphreys (1996) U.S. Pat. No. 5,559,028; Humphreys et al., (1999) U.S. Pat. No. 5,919,639, the contents of which are incorporated herein by reference). Previous experimentation with modified versions of the Ii-key peptide have indicated that a wide variety of modifications can be made to this polypeptide without detriment to activity. Indeed, modifications often enhanced antigen presentation activity of the polypeptide. Results detailed in the Exemplification section below indicate that all modified Ii key peptides which retain antigen presentation enhancing activity will function in the enhancing hybrid of the present invention when appropriately incorporated. Modifications of the Ii key peptide include deletion of one or more amino acids from the N-terminus, deletion of one or more amino acids from the C-terminus, protection of the N-terminus, amino acid substitutions, and introduction of cyclical peptides. Deletions of the Ii key peptide which retain at least 4 contiguous amino acids of the original sequence, or a substituted version thereof, exhibit functional activity. Various natural or non-natural amino acids may be substituted at respective residue positions. Some examples of molecules which may be substituted are peptidomimetic structures, D-isomer amino acids, N-methyl amino acids, L-isomer amino acids, modified L-isomer amino acids, and cyclized derivatives. In addition, procedures of medicinal chemistry may be applied by one skilled in the art using routine experimental methods to obtain additional modifications of the N-terminal segment of hybrids. Examples of such procedures are methods of rational drug design, molecular modeling based on structural information from X-ray diffraction data, nuclear magnetic resonance data, and other computational methods, and screening of products of combinatorial chemical syntheses, and isolations of natural products. Examples of modified versions of Ii key peptide which are known to retain high activity are LRMK (SEQ ID NO: 3), LRMKLPK (SEQ ID NO: 4), LRMKLPKS (SEQ ID NO: 5), LRMKLPKSAKP (SEQ ID NO: 6), and LRMKLPKSAKPVSK (SEQ ID NO: 7). Other modifications and modified versions of the Ii-key peptide are described in Humphreys et al., (1999) U.S. Pat. No. 5,919,639, and in Humphreys (1996) U.S. Pat. No. 5,559,028. A modified version of the Ii-key peptide (YRMKLPKPPK-PVSKMR, SEQ ID NO: 2) which is known to retain activity is referred to herein as an 'Ii-key homolog'. The term Ii key homolog as used herein is inclusive of the Ii key peptide itself.

The 'antigenic epitope' of the enhancing hybrid is an epitope which is presented by some allele of some MHC class II molecule to some T cell. As such, the antigenic epitope binds to the antigenic peptide binding site of an MHC class II molecule. An 'antigenic epitope' selected for use in the generation of an enhancing hybrid of the present invention may be further modified for use. That is to say, polypeptides of natural or modified sequence, peptidomimetic structures, and also chemical structures which are not natural or modified amino acids may be included in the antigenic epitope. In addition, various chemical modifications may be made to the antigenic epitope, for example, the addition in whole or in part of non-natural amino acids, or of other backbone or side chain moieties, wherein the modifications preserve binding of the antigenic epitope in the antigenic peptide binding site of mammalian MHC class II molecule in a manner favorable for T cell stimulation. Such chemical structures might bear moderate, little, or no apparent structural resemblance to any antigenic peptide which is derived from a natural protein sequence. Such modifications might or might not bear on recognition by T cell receptors. Modifications may increase recognition of the antigenic epitope (e.g. lead to recognition by previously non-recognizing subsets of T cell receptors).

The intervening chemical segment in the hybrid or 'spacer' links the Ii-key homolog and the antigenic epitope. Two or more such intervening segments are termed 'spacers'. The spacer is composed of a covalently joined group of atoms ranging from zero to a number of atoms which, when arranged in a linear fashion, would extend up to the length of peptidyl backbone atoms of 20 amino acids, likewise arranged in a linear fashion. Preferably, the spacer is less than the length of a peptidyl backbone of 9 amino acids linearly arranged. Optimally, spacer length is the length of a peptidyl backbone of between 4 and 6 amino acids, linearly arranged. Preferably, the spacer is unable to hydrogen bond in any spatially distinct manner to the MHC class II molecule.

Various chemical groups may be incorporated in the spacer segment instead of amino acids. Examples are described in Tournier et al., (1999) U.S. Pat. No. 5,910,300, the contents of which are incorporated herein by reference. In a preferred embodiment the spacer is comprised of an aliphatic chain optimally interrupted by heteroatoms, for example a $C_2$–$C_6$ alkylene, or =N—$(CH_2)_{2-6}$—N=. Alternatively, a spacer may be composed of alternating units, for example of hydrophobic, lipophilic, aliphatic and aryl-aliphatic sequences, optionally interrupted by heteroatoms such as O, N, or S. Such components of a spacer are preferably chosen from the following classes of compounds: sterols, alkyl alcohols, polyglycerides with varying alkyl functions, alkyl-phenols, alkyl-amines, amides, hydrophobic polyoxyalkylenes, and the like. Other examples are hydrophobic polyanhydrides, polyorthoesters, polyphosphazenes, polyhydroxy acids, polycaprolactones, polylactic, polyglycolic polyhydroxy-butyric acids. A spacer may also contain repeating short aliphatic chains, such as polypropylene, isopropylene, butylene, isobutylene, pentamethlyene, and the like, separated by oxygen atoms.

Additional peptidyl sequences which can be used in a spacer are described in Whitlow et al., ((1999) U.S. Pat. No. 5,856,456) the contents of which are incorporated herein by reference. In one embodiment, the spacer has a chemical group incorporated within which is subject to cleavage. Without limitation, such a chemical group may be designed for cleavage catalyzed by a protease, by a chemical group, or by a catalytic monoclonal antibody. In the case of a protease-sensitive chemical group, tryptic targets (two amino acids with cationic side chains), chymotryptic targets (with a hydrophobic side chain), and cathepsin sensitivity (B, D or S) are favored. The term 'tryptic target' is used herein to describe sequences of amino acids which are recognized by trypsin and trypsin-like enzymes. The term 'chymotryptic target' is used herein to describe sequences of amino acids which are recognized by chymotrypsin and chymotrypsin-like enzymes. In addition, chemical targets of catalytic monoclonal antibodies, and other chemically cleaved groups are well known to persons skilled in the art of peptide synthesis, enzymic catalysis, and organic chemistry in general, and can be designed into the hybrid structure and synthesized, using routine experimental methods.

The hybrids of the present invention vary from totally peptide in character to substantially non-peptide in character. In view of the fact that some homologs are substantially reduced or non-peptide in character, they will be more likely to have favorable properties, for example, penetration through cellular membranes, solubility, resistance to proteolysis, resistance to inactivation by conjugation, oral bioavailability, and longer half life in vivo.

Also included within the scope of this invention are pharmaceutically acceptable salts of the hybrid molecule, when an acidic or basic group is present in the structure. The term 'pharmaceutically acceptable salt' is intended to include all acceptable salts such as acetate, ammonium salt, benzenesulfonate, benzoate, borate, bromide, calcium edetate, camsylate, carbonate, chloride/dihydrochloride, citrate, clavulanate, edetate, edisylate, estolate, esylate, fumarate, hexylresorcinate, hydrabamine, hydroxynaphthoate, iodide, isothionate, lactate, lactobionate, laurate, mesylate, methylbromide, methylnitrate, methylsulfate, mucate, napsylate, nitrate, N-methylglucamide, oleaste, oxalate, pamoate, palmitate, panoate, pantothenate, phosphate/diphosphate, polygalacturonate, subacetate, sulfate, tartrate, tosylate, triethiodide, valerate, and the like. The pharmaceutically acceptable salt can be used as a dosage form for modifying the solubility or hydrolysis characteristics, or can be used in a sustained release or pro-drug formulation. Depending on the particular functionality for the compound of the present invention, pharmaceutically acceptable salts of the compounds of this invention may be formed from cations such as sodium, potassium, aluminum, calcium, lithium, magnesium, zinc and from bases such as ammonia, arginine, chloroprocaine, choline, diethanolamine, diethylamine, ethylenediamine, lysine, N-methyl-glutamine, ornithine, N,N'-dibenzylethylenediamine, N-benzylphenethylamine, piperazine, procaine, tris(hydroxymethyl)aminomethane, and tetramethylenediamine hydroxide, and the like. These salts may be prepared by standard procedures, for example, by reacting a free acid with suitable organic or inorganic base. When a basic group is present, such as an amino, and acidic salt, i.e., acetate, hydrobromide, hydrochloride, pamoate, and the like, can be used as the dosage form.

Also in the case of an acid (—COOH) or alcohol group being present, pharmaceutically acceptable esters can be employed, for example, acetate, maleate, pivaloyloxymethyl, and the like and those esters known in the art for modifying solubility or hydrolysis characteristics for use as sustained release or prodrug formulations.

The hybrid molecules of this present invention or components thereof may have chiral centers, and therefor may occur as racemates, racemic mixtures, and as individual enantiomers or diastereomers, with all such isomeric forms being included in the present invention as well as mixtures thereof. Furthermore, some of the crystalline forms of hybrid compounds of the present invention may exist as polymorphs and as such are intended to be included in the present invention. In addition, some of the compounds of the present invention may form solvates with water or common organic solvents. Such solvates are also encompassed within the scope of this invention.

The enhancing hybrid of the present invention may be composed of peptide or peptidomimetic or additional chemical groups which may be synthesized and selected by methods which have been developed for the synthesis and selection of antigenic peptides. Those methods and compounds are presented in the following patents: Geysen et al., (1987) U.S. Pat. No. 4,708,871; Geysen et al., (1993) U.S. Pat. No. 5,194,392; Schatz et al., (1993) U.S. Pat. No. 5,270,170; Lam et al., (1995) U.S. Pat. No. 5,382,513; Geysen et al., (1996) U.S. Pat. No. 5,539,084; Pinilla et al., (1996) U.S. Pat. No. 5,556,762; Geysen et al., (1997) U.S. Pat. No. 5,595,915; Kay et al., (1998) U.S. Pat. No. 5,747,334; and Nova et al., (1999) U.S. Pat. No. 5,874,214, the contents of which are incorporated herein by reference.

The activity of a hybrid is determined in one or more of a series of immunological assays which detect an effect on the recognition of an antigenic peptide sequence by a T cell. Experiments detailed in the Exemplification section below demonstrate the utility of incorporating the antigenic epitope IAYLKQATAK-NH$_2$ (SEQ ID NO: 8) into the following hybrids: Ac-LRMK(SEQ ID NO: 2)-5-aminopentanoyl-IAYLKQATAK(SEQ ID NO: 8) —$NH_2$; Ac-LRMK(SEQ ID NO: 2)-5-aminopentanoyl-5-aminopentanoyl-IAYLKQATAK(SEQ ID NO: 8) —$NH_2$; Ac-LRMKLPKSIAYLKQATAK-$NH_2$ (SEQ ID NO: 9); Ac-LRMKLPKSAKPIAYLKQATAK-$NH_2$ (SEQ ID NO: 10); and Ac-LRMKLPKSAKPVSKIAYLKQATAK-$NH_2$ (SEQ ID NO: 11). Each of these hybrids was shown to stimulate the responding T cell hybridoma with higher efficacy than the unincorporated antigenic epitope Ac-IAYLKQATAK-$NH_2$ (SEQ ID NO: 8). This determination was made by measuring the binding of the hybrids and the antigenic epitope, to an antigen presenting cell as a function of concentration, followed by recognition by a T cell hybridoma having a T cell receptor which recognizes the epitope bound into the antigenic peptide binding site of the MHC class II molecule of the antigen presenting cell. The antigen presenting cell used was the CH27 cell line and the T cell hybridoma used was the Tpc9.1 T hybridoma cell line. Additional details of the experimental method are presented in the Exemplification below.

These results demonstrate that each of the hybrids tested has considerably greater activity than the control antigenic epitope. Specifically the endpoint for half maximal stimulation from the unincorporated antigenic epitope is about 20 nM. The endpoint for half maximal stimulation with hybrids Ac-LRMKLPKSAKPIAYLKQATAK-$NH_2$ (SEQ. ID. NO: 10) and Ac-LRMK(SEQ ID NO: 3)-5-aminopentanoyl-5-aminopentanoyl-IAYLKQATAK(SEQ ID NO: 8) —$NH_2$ is about 50 pM. The activity of hybrids using a methylene spacer is comparable to those with the natural sequence of the Ii protein. These experiments demonstrate the efficacy of hybrids of Ii-Key core sequence and antigenic epitopes in vitro, and indicate that the antigen presentation efficacy of an antigenic epitope which binds to the antigenic peptide binding site of an MHC class II molecule is increased upon incorporation into an enhancing hybrid of the present invention. They also demonstrate that a peptide sequence derived from the primary sequence of Ii protein, in registry with the Ii Key sequence is not needed, and furthermore is not optimal.

Additional assay systems can be used to measure the effect of incorporating an antigenic epitope into an enhancing hybrid of the present invention. Assays with alternative readouts for recognition of antigenic epitopes in MHC class II molecules include, without limitation, measuring efficacy of immunoglobulin production from B cells, measuring efficacy of cytotoxic T cell generation, and the use of native T cells from animals which are outbred, inbred, congenic, transgenic for a T cell receptor or another biologically relevant molecule.

The presence of an enhancing hybrid of the present invention also has the activity of inhibiting or modulating the T cell response to other antigenic epitopes present by dislocating epitopes which are bound to the MHC class II molecule. In this respect, the hybrid also functions as a general inhibitor of MHC class II restricted antigen presentation with regard to all other antigenic epitopes. In this respect, the hybrid may also be referred to as an "MHC class II antigen presentation inhibiting hybrid polypeptide" or simply as an "inhibiting hybrid".

A molecule which binds into the MHC class II molecule antigen binding site, which does not have T cell stimulating activity is considered to be a blocker of the antigenic peptide binding site of such MHC class II molecules in which it binds. Binding of the blocker inhibits or disengages binding of antigenic epitopes present. Such a molecule has value as an immunosuppressant. An inhibiting hybrid of the present invention can also be made by incorporating a blocker into the location which is usually occupied by an antigenic epitope. Incorporation of the blocker into an inhibiting hybrid enhances the inhibitory activity of the blocker. The term 'antigen binding site ligand' is used herein to refer to a molecule which binds into the MHC class II molecule antigen binding site. This term encompasses both antigenic epitopes and non-antigenic molecules.

Similar parameters apply to the physical requirements of an antigen binding site ligand which is used to generate an inhibiting hybrid, as those listed above for an antigenic epitope. The antigen binding site ligand used to generate an inhibiting hybrid is defined herein to include any peptide sequence of natural or modified sequence, or of peptidomimetic sequence, or of a chemical structure not including natural or modified amino acids, which has a character demonstrated or considered to bind into a mammalian MHC class II molecule, whole or partly in the space shown to be occupied by known antigenic peptides which are recognized by some T cells. An antigen binding site ligand need not be comprised of only natural amino acids, but can be comprised of various modifications, for example, in whole or in part of non-natural amino acids, or of other backbone or side chain moieties, which modifications lead to binding suitably in the antigenic peptide binding site of mammalian MHC class II molecules, in a manner to effect a desired result. Such chemical structures might bear moderate, little, or no apparent structural resemblance to any antigenic peptide which is derived from a natural protein sequence.

The antigen binding site ligand which has inhibitory activity when incorporated into a hybrid of the present invention may be one of the compounds described in, or discovered through the use of the methods in one or more of the following group of patents, the contents of which are incorporated herein by reference: Sette et al., (1998) U.S. Pat. No. 5,736,142; Adams et al., (1998) U.S. Pat. No. 5,817,757; Gaeta et al., (1997) U.S. Pat. No. 5,679,640; Kubo et al., (1997) U.S. Pat. No. 5,662,907; Robbins et al., (1998) U.S. Pat. No. 5,843,648; and Kawakami et al., (1998) U.S. Pat. No. 5,844,075.

Assays can be designed by one of skill in the art to measure the effect of inhibition or modulation of a T cell response to another antigenic epitope (e.g. a standard or control antigenic epitope) by an inhibiting hybrid of the present invention, using routine experimental procedures. In such assays, the inhibiting hybrid is added to the standard assay mixture either before, concurrent, or subsequent to the addition of the other antigenic epitope. When addition of the hybrid occurs before or after addition of the other antigenic epitope, hybrid may be administered more than once. Such additional assays have utility under varying circumstances, for example, the detection of optimal hybrid structure leading to inhibition of an immune response, or optimal hybrid structure leading to expulsion of an endogenously processed and charged antigenic peptide, with replacement by a synthetic peptide, under physiological conditions.

Another aspect of the present invention is a method for the identification of a molecule which functions in an equivalent fashion as the Ii key peptide within the context of an enhancing hybrid of the present invention. Such molecules include novel Ii key homologs, and may also include seemingly unrelated molecules. Such molecules are obtained and identified, for example, from libraries of compounds (e.g. libraries of molecules from natural sources, or molecules produced by combinatorial chemistry synthesis). To that end, libraries of candidate molecules are prepared and each molecule in that library is joined covalently through an appropriate spacer to the N-terminus of an antigenic epitope, to form a candidate hybrid. When combinatorial libraries of peptides are used as candidate molecules, each amino acid of the candidate molecule N-terminal segment of the hybrid can be added to the N-terminal segment of the hybrid in the course of synthesis in a C to N direction starting from the C-terminal amino acid residue of the hybrid sequence by automated methods of synthesis. In the case of peptidomimetic syntheses, for example by the methods revealed in the patents listed above, routine experimental methods of polymer synthesis are used. In the case of combinatorial chemical syntheses of organic ring-based compounds, such compounds are joined covalently by a spacer to the antigenic peptide. Examples of such organic ring-based compounds, which can be prepared in libraries of homologs, are revealed in the following patents, the contents of which are incorporated herein by reference: Valerio et al., (1997) U.S. Pat. No. 5,627,210; Houghten et al., (1998) U.S. Pat. No. 5,783,577; Nefzi et al., (1998) U.S. Pat. No. 5,786,448; Ostresh et al., (1999) U.S. Pat. No. 5,856,107; and Meyer et al., (1999) U.S. Pat. No. 5,859,190. Additional modifications can be identified by methods of rational drug design, screening of products of combinatorial chemical syntheses, and screening of isolations from natural sources, through routine experimentation by one skilled in the art.

The antigenic epitope for use in this method should conform to the above description of an antigenic epitope. Preferably, an antigenic epitope is used for which a reliable T cell hybridoma response assay is available (e.g. pigeon cytochrome C epitope). The spacer for use in this method should also conform to the above description of a spacer.

Once candidate molecules are appropriately linked to an antigenic epitope, the hybrid produced is tested for antigen presentation enhancing activity using a T cell hybridoma response assay which is specific for the antigenic epitope presented by an antigen presenting cell in the context of an MHC class II molecule. Hybrids which have antigen presentation enhancing activity are identified by this assay, with identification of a hybrid being an indication that the corresponding candidate molecules which are incorporated within the N-terminus of the identified hybrid functions in an equivalent fashion to the Ii key peptide within this context. This method can also be adapted for use in identifying specific molecules (e.g. molecules produced by rational design) which also function in an equivalent fashion to the Ii key peptide. Such a molecule would simply be incorporated into the appropriate hybrid and then the hybrid tested for antigen presentation enhancing activity as described above.

The present invention also encompasses the molecule which functions within the context of an MHC class II antigen presentation enhancing hybrid, identified by the above described method, and also all enhancing hybrids which incorporate the molecule.

In another respect, the present invention relates to a method for enhancing presentation of an MHC class II restricted antigenic epitope to a T lymphocyte. In this method, the MHC class II restricted antigenic epitope is appropriately incorporated into the C-terminus of an enhancing hybrid of the present invention, described above. The produced enhancing hybrid is then contacted under physiological conditions to an MHC class II expressing antigen presenting cell which is in contact with or is then contacted to a T cell which is responsive to the presentation of the antigenic epitope by an MHC class II molecule of the antigen presenting cell. This method is suitable for use with all antigenic epitopes which conform to the above listed description of an antigenic epitope. Examples of methods to assay such enhancement in vitro are detailed in the Exemplification section below, and in U.S. Patents listed in the present disclosure.

The method of enhancing presentation of an MHC class II restricted antigenic epitope to a T lymphocyte finds wide application in the diagnosis and therapy of diseases. T cell responses to diagnostic antigenic epitopes are often measured in the diagnosis of diseases, particularly with respect to etiological infectious agents. The use of enhancing hybrids of the present invention which have such diagnostic antigenic epitopes incorporated will increase substantially the sensitivity of these in vi tro diagnostic assays. In the case of infectious diseases and cancer, antigenic epitopes which are identified as pathogen or cancer specific can be incorporated into an enhancing hybrid of the present invention and the hybrid then used to initiate a Th response to a pathogen or cancer specific MHC class II-presented antigenic epitope. This response leads to activation and expansion of T helper cells which in turn activate or 'license' dendritic cells, to prime an effective MHC class I restricted cytotoxic T lymphocyte response toward the invading organism. In the case of autoimmune diseases, allergy, and graft rejection, specific antigenic epitopes which trigger the pathogenic immune response are identified and then incorporated into an enhancing hybrid of the present invention. The hybrid is then used to stimulate T cells in a manner leading to a Th2 response which will down regulate T cell responses. In this case, stimulation of a suppressor cell response is used to down regulate a pathogenic immune response. Methods for identifying enhancing hybrids which specifically stimulate a predetermined subset of T lymphocytes are described below. Additional methods and utilities of such hybrids in the therapy of disease are considered below.

In another respect the present invention relates to a method for identifying a specific antigenic epitope which stimulates given (predetermined) T lymphocytes, or clonal cells derived therefrom, using combinatorial chemistry procedures for peptide synthesis. The increased sensitivity of MHC class II restricted T cell stimulation which is produced by the enhancing hybrid of the present invention, makes feasible the screening of a large number of different molecules for T cell stimulatory activity with a given T lymphocyte. In the method, a library of candidate peptides or compounds is provided or synthesized. Each candidate compound in the library is independently joined at its N-terminus to a mammalian Ii key homolog, described above, by a covalent linkage through a spacer, also described above, to produce a hybrid resembling an enhancing hybrid of the present invention. Each of these hybrids is then tested for the ability to stimulate the predetermined T lymphocyte when presented in the context of an MHC class II molecule of an antigen presenting cell. This can be accomplished by contacting each respective hybrid product with an antigen presenting cell and the T lymphocyte which will respond to the appropriate antigenic epitope presented in the context of a MHC class II molecule of the antigen presenting cell. In a preferred embodiment, such assays are performed on a large scale to screen a high number of candidates. Hybrids which are determined to stimulate the T lymphocyte when presented by the antigen presenting cell, by definition contain an antigenic epitope which stimulates the T lymphocyte.

Candidate compounds may be obtained from a variety of sources, for example, libraries of naturally available molecules and also combinatorial chemistry libraries. In one embodiment, the process of synthesis of the candidate compounds is extended upon to produce the necessary hybrids. In many cases such libraries are designed with certain sets of possible sequences defining one or a few amino acids in certain sequence positions. In the course of the synthesis of those peptides, which follows in a C to N direction, one or more residues of the spacer sequence are added, followed by addition of the desired residues of the Ii key, N-terminal segment. The candidate compound may be composed of any materials or components identified above as potential materials or components for antigenic epitopes as defined herein. Optimally, a candidate compound is a polypeptide or peptidomimetic structure which is predicted to bind into the antigenic peptide binding site of an MHC class II molecule.

The present invention is also intended to encompass the specific antigenic epitope which is identified by this method. Also encompassed is an enhancing hybrid into which this specific antigenic epitope has been incorporated.

Candidate compounds may also be obtained by an in vitro method for generation of diversity at a genetic level, followed by expression of the polypeptidyl sequences. Compounds which are identified by the above screen can be used as the basis for additional sublibraries which are screened in the same or additional assays. Various methods may be used to generate diversity of antigenic epitope sequences, such as phage display, ribosome display, and in vitro RNA-protein fusion technology. Such methods are in part presented in the following patents, the contents of which are incorporated herein by reference: Huang et al., (1996) U.S. Pat. No. 5,516,637; Garrard et al., (1998) U.S. Pat. No. 5,821,047; Kay et al., (1998) U.S. Pat. No. 5,852,167; Collines et al., (1998) U.S. Pat. No. 5,925,559. Some of these methods are also presented in part in the following publications: Roberts et al., (1997) Proc. Natl. Acad. Sci. U.S.A. 94: 12297; Hanes et al., (1998) Proc. Natl. Acad. Sci. U.S.A. 95: 14130; Jermutus et al., (1998) Curr. Opin. Biotechnol. 9: 534. Relative to these methods, one process entails introduction of the sequence LRMK (SEQ ID NO: 3), and modifications thereof, into the polypeptidyl product by genetic methods. The positioning of the LRMK (SEQ ID NO: 3) motif in the linear sequence of that product is appropriately separated using a spacer described above, with respect to the antigenic epitope. Routine experimental methods for the creation, expression and analysis of the polypeptidyl products, and for the selection of one or more polypeptidyl products with favorable properties, are well know to those skilled in the art.

In addition to increasing the overall efficacy of presentation of an antigenic epitope by an antigen presenting cell, incorporating an antigenic epitope in an enhancing hybrid of the present invention can also enhance the range of MHC class II alleles for which an allelically restricted antigenic epitope is presented. An increased allelic range of the enhancing hybrid versus the antigenic epitope is detected by performing the above described assay procedures with antigen presenting cells which express a range of MHC class II alleles. The range of MHC class II alleles should reflect the desired range. Examples of such assay systems for multiple alleles of MHC class II molecules are presented in R. Humphreys, (1996) U.S. Pat. No. 5,559,028, and Humphreys et al., (1999) U.S. Pat. No. 5,919,639, the contents of which were incorporated above. Hybrids which exhibit greatest activity with the desired range of MHC class II alleles are selected for use. The predetermined range of allelic activity may have a relationship to known diseases or other medical conditions. In a preferred embodiment, the range of MHC class II alleles is selected from the HLA-DR alleles associated with rheumatoid arthritis, multiple sclerosis, insulin-dependent diabetes mellitus. Such selections of HLA-DR alleles, and the choice of antigen presenting cell lines, and T cell lines and hybridomas to assay for reactivities on such alleles, are readily ascertained by one skilled in the art, using readily available materials and routine experimental conditions.

In another aspect, the present invention relates to a method for identifying or selecting an antigenic epitope which exhibits a predetermined pattern of MHC class II restricted Th1 and Th2 stimulation. The desired predetermined pattern of stimulation may be the stimulation of only Th1, or only Th2, or stimulating both Th1 and Th2, responses in presenting an MHC class II restricted antigenic peptide to a T cell. Candidate antigenic epitopes are appropriately incorporated into an antigen presentation enhancing hybrid polypeptide of the present invention. Enhancing hybrids which exhibit presentation activity, with the desired pattern of MHC class II restricted TH1 and Th2 stimulation are then identified from the enhancing hybrids generated. Screening for hybrid molecules which exhibit the desired activity is accomplished by contacting the hybrid polypeptide with an MHC class II expressing antigen presenting cell and a T cell which is responsive to the presentation of the antigenic epitope by an MHC class II molecule of the antigen presenting cell. Contact of the hybrid and the cells should occur under physiological conditions. Procedures for the assay of TH1 and Th2 responses can be executed as described in the following patents, the contents of which are incorporated herein by reference: Daynes et al., (1996) U.S. Pat. No. 5,540,919; Powrie et al., (1997) U.S. Pat. No. 5,601,815; Metzger et al., (1997) U.S. Pat. No. 5,665,347; Hsu et al., (1998) U.S. Pat. No. 5,776,451; Sedlacek et al., (1998) U.S. Pat. No. 5,830,880; Daynes et al., (1998) U.S. Pat. No. 5,837,269; Reed (1999) U.S. Pat. No. 5,879,687; Wang (1999) U.S. Pat. No. 5,895,646; Baumann et al., (1999) U.S. Pat. No. 5,897,990; and Levitt et al., (1999) U.S. Pat. No. 5,908,839.

TH1 and Th2 stimulation are generally determined by cytokine release assays. Enhancing hybrids which exhibit greatest activity in producing the cytokine release which correlates to the desired TH1 and/or Th2 stimulation pattern are identified and selected for use. In a preferred embodiment, the predetermined pattern of cytokine release reflects a pattern associated with enhancement or suppression of disease or other physical conditions. For example, hybrids are preferred which produce cytokine release patterns associated with autoimmune diseases such as rheumatoid arthritis, multiple sclerosis, or insulin-dependent diabetes mellitus. In addition, hybrids may be selected for favorable effects on the cytokine release patterns associated with infectious diseases and allergies. The choice and execution of the appropriate assays to determine TH1 and Th2 stimulation, including both animal experimentation and attendant in vitro assays of responses in those animals, and including other in vitro assays, are readily ascertained by one skilled in the art, using readily available materials and routine experimental conditions.

The enhancing hybrid polypeptide of the present invention can be used to modulate the immune response of an individual to a specific molecule, by enhancing the MHC class II presentation of an antigenic epitope of the molecule to T lymphocytes of the individual. Modulation of the immune response may be enhancement or suppression, and corresponds to the subset of T lymphocytes, T-helper or T-suppressor respectively, which are stimulated. Which lymphocytes are stimulated is determined by the specific enhancing hybrid administered, the specific hybrid being selected for the desired T lymphocyte stimulation pattern, described above. Once the appropriate enhancing hybrid is generated and selected, it is administered to the individual under conditions appropriate for the delivery of the hybrid to the antigen presenting cells of the individual. A pharmaceutically acceptable carrier may be used for appropriate delivery of the enhancing hybrid. Suitable formulations of the enhancing hybrid of the present invention include, without limitation, topical, oral, systemic and parenteral pharmaceutical formulations. Formulations and methods and doses of administrations are discussed in more detail below.

The method for modulating the immune response of an individual, described above, finds use in the therapeutic treatment of an individual with a disease or condition. An antigenic epitope to which an enhanced immune response is considered to be beneficial in treatment of the patient is first selected. In one embodiment, the molecule from which the antigenic epitope is derived plays a role in pathogenesis. Alternatively, the antigenic epitope may be an epitope found on a harmful agent such as a pathogen, or on a pathogen infected cell. The term 'therapeutic treatment' as used herein is intended to include ameliorating the signs or symptoms of disease, or arresting the progression of disease in an individual identified or considered to be suffering from a disease. The term 'prevention' as used herein is intended to include ameliorating the underlying cause to, or associated factor predisposing to, a disease, in an individual who might not have begun to experience recognizable signs or symptoms of a disease.

The disease may be an infectious disease caused or associated with infection by a bacterium, a virus, a parasite, a fungus, a rickettsia, or other infectious agent, or combination of such agents. The therapy may be directed against the toxin of a disease. Preferred toxins for epitope derivation include, without limitation, staphylococcal enterotoxins, toxic shock syndrome toxin, retroviral antigens (e.g. antigens derived from human immunodeficiency virus), streptococcal antigens, mycoplasma, mycobacterium, and herpes viruses. Highly preferred toxins are SEA, SEB, $SE_{1-3}$, SED and SEE.

The disease or condition may be considered to be an autoimmune process, for example rheumatoid arthritis, multiple sclerosis, lupus erythematosus, diabetes mellitus, myasthenia gravis, autoimmune thyroiditis, scleroderma, dermatomyositis, pemphigus, and other similar processes. Examples of such model systems for autoimmune diseases which can be used to evaluate the effects of the compounds and methods of the present invention are systemic lupus erythematosus, myasthenia gravis, rheumatoid arthritis, insulin dependent diabetes mellitus, and experimental allergic encephalomyelitis. The procedures for conducting these experiments are presented in Clark et al., (1994) U.S. Pat. No. 5,284,935, the contents of which are incorporated herein by reference.

The disease or condition may be considered to be an allergic process, for example asthma, hayfever, allergic rhinitis, topical dermatitis, colitis, and other such processes initiated or associated with particular allergens or no defined allergen. Examples of such allergens are plant, animal, bacterial, parasitic allergens and metal-based allergens that cause contact sensitivity. Preferred allergens for use in the present invention are weed, grass, peanut, mite, flea and cat antigens.

Alternatively, the disease or condition may be a proliferative or malignant process, for example cancer, benign prostatic hypertrophy, psoriasis, adenomas or other cellular proliferations of intrinsic origin, or in response to a viral or other infectious, irritative, or environmental process.

The term 'mammal' as used herein is meant to encompass the human species as well as all other mammalian species. The compounds and methods of this invention may be applied in the treatment of diseases and conditions occurring in individuals of all mammalian species. The term 'individual' as used herein refers to one of any mammalian species, including the human species. The diseases and conditions occurring in individuals of the human species, and mentioned herein by way of example, shall include comparable diseases or conditions occurring in another species, whether caused by the same organism or pathogenic process, or by a related organism or pathogenic process, or by unknown or other known, organism and/or pathogenic process. The term 'physician' as used herein also encompasses veterinarians, or any individual participating in the diagnosis and/or treatment of an individual of a mammalian species.

The present invention also provides for the administration of a compound, as a drug, a prodrug of the compound, or a drug-metabolite of the compound, in a suitable pharmaceutical formulation. The terms 'administration of' or 'administering a' compound is understood to mean providing a compound of the invention, as a drug; a prodrug of the compound, or a drug-metabolite of the compound, to an individual in need of treatment or prevention of a disease. Such a drug which contains one or more of the hybrid polypeptides of the present invention, as the principal or member active ingredient, for use in the treatment or prevention of one or more of the above-noted diseases and conditions, can be administered in a wide variety of therapeutic dosage forms in the conventional vehicles for topical, oral, systemic, and parenteral administration. The route and regimen of administration will vary depending upon the disease or condition to be treated, and is to be determined by the skilled practitioner. For example, the compounds can be administered in such oral dosage forms for example as tablets, capsules (each including timed release and sustained release formulations), pills, powders, granules, elixirs, tinctures, solutions, suspensions, syrups and emulsions, or by injection. Likewise, they may also be administered in intravenous (either by bolus or infusion methods), intraperitoneal, subcutaneous, topical with or without occlusion, or intramuscular form. All of these forms are well known to those of ordinary skill in the pharmaceutical arts.

The daily dose of the products may be varied over a range from 0.001 to 1,000 mg per adult per day. For oral administration, the compositions are preferably provided in the form of tables containing from 0.001 to 1,000 mg, preferably 0.001, 0.01, 0.05, 0.1, 0.5, 1.0, 2.5, 10.0, 20.0, 50.0, 100.0 milligrams of active ingredient for the symptomatic adjustment of dosage according to signs and symptoms of the patient in the course of treatment. An effective amount of drug is ordinarily supplied at a dosage level of from about 0.0001 mg/kg to about 50 mg/kg of body weight per day. The range is more particular from about 0.0001 mg/kg to 7 mg/kg of body weight per day.

Advantageously, suitable formulations of the present invention may be administered in a single daily dose, or the total daily dosage may be administered in divided doses for example of two, three, or four times daily. The enhancing hybrid polypeptide of the present invention may be used to prepare a medicament or agent useful for the treatment of the diseases or conditions listed above. Furthermore, compounds of the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, or course, be continuous rather than intermittent throughout the dosage regimen.

For treatment and prevention of disease, the hybrid polypeptide of the present invention may be administered in a pharmaceutical composition comprising the active compound in combination with a pharmaceutically acceptable carried adopted for topical administration. Topical pharmaceutical compositions may be, for example, in the form of a solution, cream, ointment, gel, lotion, shampoo, or aerosol formulation adapted for application to the skin. These topical pharmaceutical composition containing the compounds of the present invention ordinarily include about 0.005% to 5% by weight of the active compound in admixture with a pharmaceutically acceptable vehicle.

For the treatment and prevention of disease and conditions, for example listed above, the hybrid polypeptide of the present invention may be used together with other agents known to be useful in treating such diseases and conditions. For combination treatment with more than one active agent, where the active agents can be administered concurrently, the active agents can be administered concurrently, or they can be administered separately-at staggered times.

The dosage regimen utilizing the compositions of the present invention is selected in accordance with a variety of factors, including for example type, species, age, weight, sex and medical condition of the patient, the severity of the condition to be treated, and the particular compound thereof employed. A physician of ordinary skill can readily determine and prescribe the effective amount of the drug required to prevent, counter, or arrest the progress of the disease or condition. Optimal precision in achieving concentration of drug with the range that yields efficacy either without toxicity or with acceptable toxicity requires a regimen based on the kinetics of the drug's availability to target sites. This process involves a consideration of the distribution, equilibrium, and elimination of the drug, an is within the ability of the skilled practitioner.

In the methods of the present invention, the compounds herein described in detail can form the active ingredient and are typically administered in admixture with suitable pharmaceutical diluents, excipients or carders (collectively referred to herein as 'carder materials') suitably selected with respect to the intended form of administration, that is, oral tablets, capsules, elixirs, syrups, and the like, and consistent with conventional pharmaceutical practices. For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethyl cellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, aga, bentonite, xanthan gum and the like.

The liquid forms may be suitably flavored suspending or dispersing agents such as the synthetic and natural gums, for example, tragacanth, acacia, methyl cellulose and the like. Other dispersing agents which may be employed are glycerin and the like. For parental administration, sterile suspensions an solutions are desired. Isotonic predations which generally contain suitable preservatives are employed when intravenous administration is desired.

Topical preparations containing the active drug component can be admixed with a variety of carrier materials well known in the art, such as, for example, alcohols, aloe vera gel, allatoin, glycerine, vitamins A or E oils, mineral oil, PPG2 myristyl propionate, and the like, to form, for example, alcoholic solutions, topical cleansers, cleansing creams, skin gels, skin lotions, and shampoos in cream or gel formulations.

The hybrid polypeptide of the present invention can also be administered in the form of liposome delivery systems, such as small unilamellar vesicles, large unilameller vesicles and multilamellar vesicles. Liposomes can be formed from a variety of compounds, including for example cholesterol, stearylamine, and various phosphatidylcholines.

The hybrid polypeptide or formulation thereof of the present invention may be coupled to a class of biodegradable polymers useful in achieving controlled release of a drug, for example, polylactic acid, polyepsilon caprolactone, polyhydroxy butyric acid, polyorthoesters, polyacetals, polydihyrdo-pyrans, polycyanoacrylates, and cross-linked or amphipathic block copolymers of hydrogels.

The hybrid polypeptides of the present invention and formulations thereof can be prepared using readily available starting materials, reagents and conventional synthesis procedures. In these reactions, it is also possible to make use of variants which are themselves known to those of ordinary skill in this art, but are not mentioned in greater detail herein.

As an alternative to administering the enhancing hybrid of the present invention directly to an individual to enhance the MHC class II presentation of an antigenic epitope to T lymphocytes of the individual, a population of antigen presenting cells may be obtained from the individual and treated ex vivo with the enhancing hybrid of the present invention. These cells are treated with the enhancing hybrid under conditions appropriate for binding of the hybrid to an MHC class II molecule of the antigen presenting cells. Once treated, the antigen presenting cells are administered to the individual under conditions which promote physical contact of the treated cells with T lymphocytes of the individual. As described above, the effect on the immune response, enhancement or suppression, will depend upon which subset of T cells are preferentially stimulated by the enhancing hybrid. Enhancement of the immune response may have a favorable effect upon the cytotoxic response against, for example, either a cancer cell or an infectious organism. Alternately, enhancement of the T suppressor cell response may have the effect of suppressing the immune response to a specific molecule. Such suppression may have a therapeutic effect when utilizing antigenic epitopes from etiological antigens of autoimmune diseases, for example, rheumatoid arthritis, multiple sclerosis, myasthenia gravis, or lupus erythematosus. The methods and procedures for the ex vivo treatment of cells from a patient with the compounds and methods of the present invention may be adapted from the following patents, the contents of which are incorporated herein by reference: Rosenberg (1998) U.S. Pat. No. 5,126,132; Chada et al., (1997) U.S. Pat. No. 5,693,522; Kriegler et al., (1998) U.S. Pat. No. 5,849,586; Gruber et al., (1999) U.S. Pat. No. 5,856,185; and Kriegler et al., (1999) U.S. Pat. No. 5,874,077.

In another respect, the compounds and methods of the present invention can be used under ex vivo conditions to promote the generation of cytotoxic T lymphocytes, using the compounds and methods described in Celis et al., (1998) U.S. Pat. No. 5,846,827, the contents of which are incorporated herein by reference.

Another aspect of the present invention is a method for inhibiting presentation of an MHC class II restricted antigenic peptide to a T lymphocyte. As discussed above, an antigen binding site ligand constitutes any peptide or molecule which binds into the antigenic peptide binding site of major histocompatibility class II molecules, and such a molecule may or may not have T lymphocyte stimulating activity. Linkage of an antigen binding site ligand to an Ii-key homolog, through a spacer, produces a hybrid which has enhanced activity at generally inhibiting MHC class II restricted antigen presentation. To generally inhibit presentation of MHC class II restricted antigenic epitopes to T lymphocytes, the antigen presentation inhibiting hybrid polypeptide is contacted to an MHC class II expressing antigen presenting cell displaying on its surface an MHC class II restricted T lymphocyte-presented antigenic epitope. The result of that action modulates the function of a T lymphocyte which is responsive to the presentation of the antigenic epitope by an MHC class II molecule of the antigen presenting cell.

In vitro assays to demonstrate inhibition of presentation of an antigenic epitope to T cells are presented in R. Humphreys, (1996) U.S. Pat. No. 5,559,028; and Humphreys et al., (1999) U.S. Pat. No. 5,919,639, the contents of which have been incorporated by reference. The biological activity of the hybrid, for example, the ability to inhibit antigen-specific T lymphocyte activation, may also be assayed in a variety of systems. In one exemplary protocol an excess of hybrid is incubated with an antigen presenting cell of known MHC expression, for example, HLA-DR1, and a T cell clone of known antigen specificity, for example, tetanus toxin (830–843) and MHC restriction (again, DR1), and the antigenic peptide itself (tetanus toxin(830–843)). The assay culture is incubated for a sufficient time for T cell proliferation, such as 1 to 4 days, and proliferation is then quantitated. That quantitation may be performed by pulsing with tritiated thymidine in the last 18 hours of incubation, or by transfer of supernatant fluid to a second culture of HT-2 cells, the proliferation of which depends upon interleukin release by the responding T cell and is measured by pulsing with tritiated thymidine in the last 18 hours of incubation. The percentage inhibition, compared to controls which received no inhibitor, is then calculated. The capacity of hybrids, and other inhibitors of antigen presentation, in an in vitro assay can be correlated to the capacity of such compounds to inhibit an immune response in vivo. In vivo activity may be determined in animal models, for example, by administering an antigen known to be restricted to the particular MHC molecule recognized by the peptide, and the immunomodulatory hybrid. T lymphocytes are subsequently removed from the animal and cultured with a dose range of antigen. Inhibition of stimulation is measured by conventional means, for example pulsing with tritiated thymidine, and comparing to appropriate controls. Certain experimental details are readily apparent to one skilled in the art.

The enhancement of activity produced by incorporation of the antigenic peptide binding site ligand into an inhibiting hybrid of the present invention allows for more rapid and accurate detection of the inhibitory activity. This enhanced detection enables identification of novel compounds which inhibit MHC class II antigen presentation. In this respect, the present invention relates to a method for identifying a compound which inhibits MHC class II antigen presentation. The method involves providing a library of candidate compounds which are predicted to be antigen binding site ligands, and covalently joining each candidate compound independently to mammalian Ii key homologs through a spacer, such that the Ii key homolog is at the N-terminus and the candidate compound is at the C-terminus. This product is referred to as a 'candidate antigen presentation inhibiting hybrid polypeptide' or 'candidate inhibiting hybrid'. The candidate inhibiting hybrids are then screened by contacting the individual candidate inhibiting hybrids to an antigen presenting cell expressing in some of its MHC class II molecules an antigenic peptide of a naturally occurring sequence, and a T lymphocyte responding to that antigenic epitope presented in the context of a MHC class II molecule of the antigen presenting cell (also known as a T lymphocyte activation assay). One then determines if contact of the candidate inhibiting hybrid decreases T lymphocyte activation compared to control reactions. A determination of decreased T lymphocyte activation in the assay is an indication that the candidate compound incorporated into the hybrid, and the candidate inhibiting hybrid itself, are inhibitors of MHC class II antigen presentation.

Candidate compounds for use in generation of the candidate inhibiting hybrid may be naturally produced products, combinatorially generated peptides, peptidomimetics, or other organic compounds.

The present invention also encompasses the inhibiting molecule and the inhibiting hybrid which are identified by the above described method. With respect to in vitro applications, a principal use of such inhibitors of antigen presentation will be in vivo, in clinical applications benefiting from either ejection of endogenously bound antigenic peptides with or without continuing blockade of MHC class II antigenic peptide binding sites. Such hybrids will find application in the treatment of autoimmune diseases, as discussed above.

Another aspect of the present invention relates to a therapeutic method to treat an individual with a disease by inhibiting the response of T lymphocytes specific to an antigenic epitope, by administering to the individual an inhibiting hybrid of the present invention to generally inhibit the response of T lymphocytes of the individual. Acceptable formulations and methods and regimens of administration of the inhibiting hybrid correspond to the above described formulations and methods and regimens of administration of the enhancing hybrid of the present invention.

The compounds and methods of this invention are dissimilar from those of Kappler et al., (1998) U.S. Pat. No. 5,820,866, the contents of which are incorporated herein by reference, in the fact that the antigenic peptide in the present invention is linked to a fragment of the Ii protein which binds noncovalently at a respective receptor site on the MHC class II molecule, rather than linked covalently to the N-terminus of one of the two chains of the MHC class II molecule. In addition, the present invention encompasses constructs in which the antigenic peptide is linked to other compounds which bind with suitable affinity to MHC class II molecules (not necessarily at the site for binding of Ii-key homologs), or to additional cell surface proteins, for example CD4, which interact with complexes formed by binding of a MHC Class II molecule and a T cell receptor, for example between an antigen presenting cell and a T lymphocyte. Such hybrids can be designed from structural models of the MHC class II molecules, by classical methods of drug design, or screening products of combinatorial syntheses or isolations of natural products, as described elsewhere herein.

The compounds and methods of this invention are dissimilar from those of Clark et al., (1994) U.S. Pat. No. 5,284,935, the contents of which are incorporated herein by reference, in the fact that in the compounds of that invention, a toxin is conjugated to either the MHC class II molecule or the antigenic peptide of a complex in which the antigenic peptide is covalently linked to the MHC class II molecule, for example at the N-terminus of one of the chains of the MHC class Ii molecules.

The compounds and methods of this invention are dissimilar from those of Stanton et al., (1998) U.S. Pat. No. 5,807,552, the contents of which are incorporated herein by reference, in that in the compounds of the referenced invention, the antigenic epitope is bounded by segments of amphipathic helical peptides which interact in a manner to create noncovalently bound multimers of periodically spaced antigenic epitopes.

The compounds and methods of this invention are dissimilar from those comprising antigenic epitopes substituted in the sequence of the Ii protein, in which the modified Ii sequence is expressed after transfection of a modified gene into an antigen presenting cell (Barton et al., *Internat. Immunol.* 10: 1159 (1998); Fujii et al., *Human Immunology* 59: 607 (1998); Malcherek et al., *Eur. J. Immunol.* 28: 1524 (1998); Stumptner et al., *The EMBO Journal* 16: 5807 (1997); Van Bergen et al., *Proc. Natl. Acad. Sci. USA* 94: 7499 (1997)). At the least such constructs are represented to favor the directing of intracellular transport of complex formed between the Ii protein and MHC class II molecules to a post-Golgi compartment for antigen/Ii protein processing and MHC class II peptide charging (Bakke et al., *Cell* 16: 707 (1990); Lamb et al., *J. Immunol.* 148: 3478 (1992)). The molecular and cellular biological mechanisms particular to the present invention are therefor not favorably exploited.

Given the present disclosure, routine experimentation will lead to the development of novel therapeutic methods. Although the data presented in the Exemplification section below are generated in experiments employing murine assays for biological activity, similar results will be found with human cells under in vitro and physiological conditions. Routine experimentation will allow optimization of the segment of the hybrid construct derived from the Ii-key sequence and of the spacer.

EXEMPLIFICATION

Example 1

Design and Synthesis of Hybrid Peptides with a Variable Spacer Between the Ii-Key Core Motif and an Antigenic Epitope The active core of the Ii-Key peptide and an antigenic epitope were coupled covalently in one 'hybrid' peptide. Such constructs were made in order to obtain enhanced potency and other functional benefits, in the effect of the Ii-Key structure on presentation by MHC class II molecules of the antigenic epitope incorporated in the hybrid. Several hybrids which had different spacers (length and composition) located between the two biologically active units, were generated for determination of biological activity.

The first structural issue in the design of the hybrids was the extent of the Ii-Key core peptide required for activity. The minimal active sequence of Ii-Key peptides LRMK (SEQ ID NO: 3) was used to produce the hybrids which were to be tested in the present study. This tetrapeptide was previously determined to retain at least 50% of maximal activity of any member of the series of Ii-key peptides which were tested in assays for effect on presentation of antigenic peptides by MHC class II molecules (Adams et al., *Eur. J. Immunol.* 25: 1693 (1995); Adams et al., *Arzneim. Forsch./ Drug Research* 47: 1069 (1997)). Peptides with additional residues extending from the C-terminus of LRMK (SEQ ID NO: 3), in the sequence of Ii protein, have been previously determined to exhibit greater activities in the basic assay for enhancement of peptide charging into MHC class II molecules. However, for this series of homologs, the Ii-key peptide portion was held constant utilizing LRMK (SEQ ID NO: 3).

The antigenic epitope in the series of hybrid peptides was also held constant. It was the pigeon cytochrome C (PGCC) antigenic epitope PGCC 95–104, IAYLKQATAK (SEQ ID NO: 8).

The series of hybrids listed in Table I was designed to test the effects of the length and composition of the spacer on activity. The rationale for the design of this series of compounds was drawn, in part, from knowledge about how Ii protein-derived peptides and antigenic peptides bind into the antigenic peptide binding groove of MHC class II molecules. Previous X-ray crystallographic analysis gathered using an antigenic peptide from influenza virus hemagglutinin, HA(307–319) (Stern et al., Nature 378: 215–221 (1994)), and an Ii-protein-derived peptide, Ii(86–102) known as the cleaved leupeptin-induced peptide (CLIP) (Ghosh et al., Nature 378: 457–462 (1995)), has revealed the molecular orientation of two peptides in the antigenic peptide binding site of HLA-DR1, an MHC class II molecule. The position CLIP occupies in the antigenic peptide binding site was identified in a cell line deficient in the HLA-DM molecule which functions in removing weakly binding peptides, including CLIP, in exchange for more tightly binding antigenic peptides (Sette et al., Science 258: 1801 (1992); Avva et al., Immunity 1: 763–772 (1994); Sloan et al., Nature 375: 802–805 (1995); Denzin et al., Cell 82: 155–163 (1995)). The core of Ii-Key, LRMK (SEQ ID NO: 3), is distal to the N-terminus of the longest of the series of CLIP peptides which have been identified (Chicz et al., Nature 358: 764 (1992)). However, longer homologs of the series of Ii-Key peptides (extending from the C-terminus of LRMK (SEQ ID NO: 3)) overlap the primary amino acid sequence of N-termini of longer forms of CLIP.

Hybrid 6 of Table I, was a hybrid composed of the Ii-Key core sequence LRMK (SEQ ID NO: 3), extending to the C-terminus with a spacer of Ii protein residues LPKSAKPVSK (SEQ ID NO: 12), to the antigenic epitope IAYLKQATAK (SEQ ID NO: 8). This assignment of a sequence of the Ii protein to be the spacer segment of the 'hybrid of reference' was arrived at by superimposing the crystallographic images of Hybrid 6 with two respective images previously established by X-ray crystallography. Those images were those that of HA (307–319) and of CLIP bound into the HLA-DR1 MHC class II molecule binding pocket (Stern et al., Nature 378: 215–221 (1994), Ghosh et al., Nature 378: 457–462 (1995)). In those two crystallographic images the P1 hydrophobic pocket of the HLA-DR1 MHC class II molecule was filled with methionine[99] of the Ii sequence of CLIP or with Leu[87] of the HA(307–319) peptide. One can reasonably predict that Ile[95] of PGCC(95–104) would also lie in the hydrophobic P1 pocket. Thus, Hybrid 6 was composed of the sequence of the Ii protein through Lys[90] and thereafter to the C-terminus of the hybrid with the sequence of PGCC(95–104). The 'crossover' in the hybrid sequence between the sequences of the Ii protein and the antigenic peptide occurred just before the residue position expected to be bound into the P1 hydrophobic pocket of HLA-DR1.

The remaining hybrid peptides were designed from careful consideration of the secondary structure and alignment of the Ii and antigenic peptides as polyprolyl type II (PPII) helices, within the groove of the antigenic peptide binding groove. X-ray crystallographic images show that the CLIP and antigenic peptides each coil in the secondary structure of a polyprolyl type II helix. In this type of helix, the amino acid repeat frequency per turn is 3.0 amino acids, in contrast to the 3.2 amino acids per turn found in the better known α-helix. Looking along the longitudinal axis of the two types of helices, the PPII helix is 'stretched out' about twice the distance per turn as found in α-helices. PPII helices do not have the inter-turn hydrogen bonds which stabilize α-helices. That is, in an α-helix the peptidyl backbone imido proton of residue i hydrogen bonds to the peptidyl backbone carbonyl of residue i+3. Due to this internal stabilization along the turns of a peptidyl backbone, α-helices form energetically relatively strong local secondary structures. Those helices can fold within proteins both upon each other and onto other local secondary structures. In contrast, PPII configurations are employed in proteins as recognition units for protein:protein interactions. Such PPII helices are found, for example, in SR-1 domains mediating recognition by intercellular proteins of the intracellular domains of transmembranal receptors, which are altered by some cell surface event, in structure or spacing. Antigenic epitopes as recognized by T cells are also coiled as PPII structures. Such PPII structures are though to allow a wider area for display of variable side chains of the antigenic sequence than would be possible for an α-helix. This results in an equilateral pyramidal structure, wherein residues along one ridge of the helix of the antigenic peptide bind into hydrophobic pockets at the base of the antigenic peptide binding cleft in the MHC II molecule. The side chains along the other two ridges of the antigenic peptide's PPII helix are exposed in shallow pockets along the surface of the MHC molecules for interaction with the T cell receptor. Roughly twice as many atoms of side chains of the MHC Class II and TCR molecules can contact each side chain of the antigenic sequence, when that sequence is a PPII helix rather than α-helix. Within the antigenic peptide binding trough between the two anti-parallel helices, the PPII helical configuration of the bound peptide extends N-terminally at least 5 residue positions beyond the first residue of the commonly identified antigenic epitope. P[87] of the Ii sequence is characterized by X-ray crystallography at the end of the trough formed by the two anti-parallel α-helices, between which sits either CLIP or antigenic peptides.

Modeling possible interactions of the hybrid peptides bridging the Ii-Key core structure LRMK (SEQ ID NO: 3) to the antigenic epitope IAYLKQATAK (SEQ ID NO: 8), produces several hypotheses about structural requirements for interactions of atoms in the spacer of the hybrid which joins the LRMK (SEQ ID NO: 3) functional group and the antigenic epitope, with the MHC class II molecules (Table I). In one hypothesis, atoms of the side chains of the amino acids of the spacer interact optimally with specific residues of the MHC class II molecule, only when the spacer is coiled as a PPII helix. This view was tested with Hybrid 6. In that hybrid, the full 10 amino acid residues immediately C-terminal to LRMK[91] (SEQ ID NO: 3) in the sequence of Ii protein, constituted the spacer, preserving the registry between Ii protein sequences of CLIP and the HA antigenic peptide seen upon superimposing the X-ray crystallographic models. If Hybrid 6 were the only tested hybrid which was biologically active, then one could conclude that MHC class II residues in the trough distal to the first residue of the antigenic sequence must be contacted.

An alternative hypothesis is that only some of the residues in the spacer are functionally required in the hybrid peptides. Hybrid 5 (Table I) was designed so that only the first seven residues immediately C-terminal to LRMK[91] (SEQ ID NO: 3) in the sequence of Ii protein, was present as the spacer. In Hybrid 4, only the first four residues immediately C-terminal to LRMK[91] (SEQ ID NO: 3) in the sequence of Ii protein, functions as the spacer. If Hybrids 5 and 4 had activities comparable to that of Hybrid 6, then this finding would indicate that secondary structure of the intervening segment as a poly prolyl type II (PPII) helix is not critical. This finding would also prompt a search for the critical contacting residues in the MHC Class II molecules, and the presumably backbone positions (e.g. peptidyl carbonyl or imino residues) which are critical to such interactions.

Additional hybrids tested the requirement for explicit residues of the Ii protein sequence in the spacer. Finding a requirement for specific residues of the Ii protein in the spacer sequence, could support the view that such spacers must be coiled as PPII helices in their active site. In these hybrids the spacer amino acid residues were replaced with ε-amino-valeric acid ('ava') residues. Hybrid 3 contained two ava residues and Hybrid 2 contained one ava residue. These hybrid peptides were homologs, respectively, of Hybrid 5 and Hybrid 4. The linear extension of ava residue, including amino group-methylene bridge-carboxyl group, approximates the length of the backbone of a tripeptidyl unit. In the event that these 'deletion homologs', Hybrid 5 and Hybrid 4, possessed biological activity, then one could conclude that there are no functional requirements for specific interactions of side chain atoms of the spacer with the MHC class II antigenic peptide binding trough.

The hybrid peptides used in the present study were all acetylated at the N-terminus and amidated at the C-terminus, to inhibit activity of exopeptidases.

The peptides of Table I were synthesized by Commonwealth Biotechnologies, Inc., 601 Biotech Drive, Richmond Va. 23225. The purity and composition of each peptide was confirmed by HPLC separation and mass spectrometry.

Example 2

Biological Activities of Hybrid Peptides

The biological activities of the series of peptides listed in Table I were determined with the T hybridoma response assay. A T cell hybridoma which is specific to the hornworm moth cytochrome C epitope IAYLKQATAK (SEQ ID NO: 8) was stimulated with that antigenic peptide or with members of the series of hybrids of the antigenic peptide and the core Ii-Key sequence listed in Table I. The hybrids were joined with spacers of various lengths. The spacers contained either amino acids in the natural sequence of the Ii protein, or methylene ($-CH_2-$) groups of 5-amino-n-valeric acid (ava; 5-aminopentanoic acid). Cultures of an antigen presenting cell and T cell hybridoma were incubated with serial 1:4 dilutions of the antigenic peptide, from 3 μM. Response was determined by measuring tritiated thymidine uptake by an HT-2 culture to which supernatants of the antigenic stimulation culture (24 hr stimulation period) had been transferred. The endpoint for half maximal response to Hybrid 1, the antigenic peptide, was about 20 nM. The endpoint for half maximal stimulation with Hybrids 5 and 2 was about 50 pM. The activity of hybrids which had a methylene spacer, Hybrid 2 and 3, were comparable to those with the natural sequence of Ii protein. These experiments demonstrate the in vitro efficacy of hybrids between the Ii-Key core sequence and antigenic peptide.

The results of these experiments indicate that an effective therapeutic is produced from the covalent hybridization of the Ii-Key core sequence, for example LRMK (SEQ ID NO: 3), through a flexible chain to a selected antigenic epitope. The flexible chain can be extended in length from 3 to 6

TABLE I

Design of a hybrid peptides with variable spacers between the Ii-Key core motif and an antigenic epitope.

| HYBRID | From Ii | | SPACER | ANTIGEN | | SYMBOL |
|---|---|---|---|---|---|---|
| 1 | Ac- | | | IAYLKQATAK-NH$_2$ | (SEQ ID NO:8) | Δ |
| 2 | Ac-LRMK | (SEQ ID NO:3)- | ava- | IAYLKQATAK-NH$_2$ | (SEQ ID NO:8) | ○ |
| 3 | Ac-LRMK | (SEQ ID NO:3)- | ava-ava- | IAYLKQATAK-NH$_2$ | (SEQ ID NO:8) | □ |
| 4 | Ac-LRMK- | | LPKS- | IAYLKQATAK-NH$_2$ | (SEQ ID NO:9) | ● |
| 5 | Ac-LRMK- | | LPKSAKP- | IAYLKQATAK-NH$_2$ | (SEQ ID NO:10) | ■ |
| 6 | Ac-LRMK- | | LPKSAKPVSK- | IAYLKQATAK-NH$_2$ | (SEQ ID NO:11) | ▼ |

The single letter amino acid codes used in this disclosure are as follows:
A = L-alanine,
D = L-aspartate,
E = L-glutamate,
F = L-phenylalanine,
H = L-histindine,
I = L-isoleucine,
K = L-lysine,
L = L-leucine,
M = L-methionine,
N = L-asparagine,
P = L-proline,
R = L-arginine,
Q = L-glutamine,
T = L-Threonine, and
Y = L-tyrosine, Ava = 5-aminopentanoic acid [ε-amino-n-valeric acid].

peptidyl units and can be composed of simple repeating units which do not hydrogen bond in any spatially distinct manner to the MHC class II molecule. Such short, simple flexible spacers produce increased activity to longer spacers composed of specific amino acid residues, as indicated by the sub-optimal activity of Hybrid 7 which has a spacer composed of the 10 amino acids naturally present in the Ii protein between LRMK (SEQ ID NO: 3) and the putative crossover site between CLIP and an antigenic peptide, as indicated from crystallographic data.

TABLE II

Enhanced T cell proliferative response to hybrids comprising Ii Key core sequence, variable spacers, and antigenic peptide.

| Conc. | HYBRID | | | | | |
|---|---|---|---|---|---|---|
| nM | 1 | 2 | 3 | 4 | 5 | 6 |
| 3000 | 25.2 | 25.1 | 31.9 | 25.2 | 27.3 | 21.5 |
| 750 | 27.8 | 23.9 | 31.7 | 23.3 | 27.5 | 23.4 |
| 188 | 32.4 | 27.2 | 26.2 | 20.8 | 29.1 | 26.9 |
| 47 | 29.5 | 20.8 | 26.2 | 19.5 | 26.2 | 25.3 |
| 12 | 10.9 | 21.9 | 29.5 | 23.1 | 44.6 | 39.2 |
| 3 | 0.4 | 30.1 | 27.9 | 19 | 31.4 | 31.4 |
| 0.73 | 4 | 28.8 | 22.3 | 19.2 | 30.1 | 28.7 |
| 0.18 | 0 | 31.2 | 21.6 | 9.1 | 36.7 | 11.9 |
| 0.05 | 0 | 19.8 | 5.3 | 5.8 | 21.3 | 2.4 |
| 0.01 | 0 | 3.4 | 0.6 | 2.5 | 14.3 | 2.9 |

Legend to Table II. The immunological response to the antigenic epitope in thousands of counts per minute, is presented as a function of dilution factor of the hybrid (1:4) serial dilution from a 3 µM stock solution.

Experimental

For this assay the following components were added at the same time of the primary culture: (a) The hybrid peptide containing the antigenic epitope (Table I); (b) mitomycin C-treated, MHC class II-positive antigen presenting cells (APC) with the MHC class II allele required for binding of the specific antigenic peptide and its presentation to the antigenic peptide-specific T cell hybridoma; (c) MHC class II allele-restricted T cell hybridoma specific for the antigenic peptide and the MHC class II allele restricting its presentation. At the end of the incubation of this primary culture, an aliquot of its supernatant is transferred into a second culture well for incubation with an interleukin-dependent lymphoblastoid cell line. The degree of stimulation of that second indicator cell by the interleukins which had been released from the activated T cell hybridoma in the primary culture is measured by quantitating tritiated thymidine deoxyribose {[$^3$H] TdR} uptake into the DNA of the HT-2 indicator cells of that second culture.

The hybrids between Ii-Key core sequence LRMK (SEQ ID NO: 3) and PGCC95–104, pigeon cytochrome C 95–104, IAYLKQATAK (SEQ ID NO: 8) are presented by $E^k$. The peptides were dissolved in phosphate-buffered saline (PBS; 0.01 M sodium phosphate buffer, pH 7.2, 0.1 M NaCl). The solutions were sterilized by filtration. The TPc9.1 T hybridoma is specific for pigeon cytochrome C 81–104 peptide presented on the murine class II MHC allele $E^k$. The CH27 B cell lymphoma line which expresses H-$2^k$ alleles was used as the antigen presenting cell.

Antigenic peptide-specific T cell activation was measured by the following procedure. Mitomycin C-treated CH27 cells ($A^k E^k$) APC were generated by incubating $5 \times 10^6$ cells/mL for 20 min at 37° C. with 0.025 mg/mL of mitomycin C (Sigma) in Dulbecco's Modified Eagle's Medium (DMEM)/10 mM N-2(hydroxyethylpiperazine-N' [2-ethanesulfonic acid] (HEPES), followed by two washes with four volumes of DMEM-5% fetal calf serum (FCS), 10 mM HEPES. T cell hybridomas were irradiated 2200 rads before each assay.

For the primary culture assay, $5 \times 10^4$ mitomycin C-treated APC, $5 \times 10^4$ T hybridoma cells and serial 1:4 dilutions from 3 uM of the peptides containing antigenic epitopes were cultured at pH 7.2–7.4, in complete DMEM-5% FCS, 10 mM HEPES, 1× nonessential amino acids (Sigma), 1 mM sodium pyruvate, 2 mM L-glutamine, 100 U/mL penicillin G, 100 µg/mL streptomycin sulfate, $5 \times 10^{-5}$ M 2-mercaptoethanol (2-ME). Wells containing only T hybridoma cells (T)+APC were included to monitor for background T cell activation; and wells containing T+APC+antigenic peptide were included to monitor for non-specific T hybridoma activation by each AE101 series peptide. Supernatants (aliquots of 20, 40 or 75 µl) from each culture were removed after 24 h and were assayed for their effect on growth of $1 \times 10^4$ interleukin-dependent HT-2 lymphoblastoid cells (added in 140, 120 or 75 µl complete Roswell Park Memorial Institute (RPMI) 1640 buffer—5% FCS, respectively), as measured by incorporation of [$^3$H]TdR, added at 1 µCi/well during the last 5 h of a 24 h HT-2 assay. For all assays the reported value is the mean of triplicate wells, with a mean standard error of less than ±10%. Since the degree of stimulation varied among assays, usually both in the primary culture and in the secondary HT-2 indicator culture, for comparisons among assays performed at different times, standard or reference peptides were always included.

The invention claimed is:

1. A method for enhancing presentation by an MHC class II expressing antigen presenting cell of an MHC class II restricted antigenic epitope to a T cell, comprising:
   a) incorporating the MHC class II restricted antigenic epitope into an MHC class II antigen presentation enhancing hybrid polypeptide, the hybrid polypeptide comprising;
      i) an N-terminus comprising the mammalian Ii key peptide LRMKLPKPPKPVSKMR (SEQ ID NO: 1) or a truncated form thereof in which the LRMK residues are unaltered and which retains antigen presentation enhancing activity;
      ii) a C-terminus comprising the MHC class II restricted antigenic epitope in the form of a polypeptide structure which binds into the antigenic peptide binding site of an MHC class II molecule of an MHC II expressing antigen presenting cell; and
      iii) an intervening chemical structure covalently linking the N-terminal and C-terminal components of the hybrid, the chemical structure being a covalently joined group of atoms which when arranged in a linear fashion forms a flexible chain which extends up to the length of 20 amino acids likewise arranged in a linear fashion; and
   b) contacting under physiological conditions:
      i) the hybrid polypeptide of step a);
      ii) the MHC class II expressing antigen presenting cell; and
      iii) a T cell which is responsive to the presentation of the antigenic epitope by the MHC class II molecule of the MHC II expressing antigen presenting cell.

2. The method of claim 1 wherein an MHC class II allelic response to the antigenic epitope is increased.

3. A method for enhancing the range of MHC class II allelic presentation of an allelically restricted antigenic epitope, comprising:
   a) incorporating the antigenic epitope into an antigen presentation enhancing hybrid polypeptide, the hybrid polypeptide comprising:
      i) an N-terminus comprising the mammalian Ii key peptide LRMKLPKPPKPVSKMR (SEQ ID NO: 1) or a truncated form thereof comprising at least the LRMK core sequence (SEQ IN NO.: 3), wherein said N-terminus retains antigen presentation enhancing activity;
      ii) a C-terminus comprising the antigenic epitope;
      iii) an intervening chemical structure covalently linking the N-terminal and C-terminal components of the hybrid, the chemical structure being a covalently joined group of atoms which when arranged in a linear fashion forms a flexible chain which extends up to the length of 20 amino acids likewise arranged in a linear fashion; and
   b) contacting the antigen presentation enhancing hybrid polypeptide of step a) with antigen presenting cells and T lymphocytes which are responsive to the presentation of the antigenic epitope by an MHC class II molecule of the antigen presenting cells, under physiological conditions.

* * * * *